(12) United States Patent
Zhou et al.

(10) Patent No.: US 8,779,177 B1
(45) Date of Patent: Jul. 15, 2014

(54) METHOD FOR BOTTOM-UP GRAPHENE SHEET PREPARATION AND BANDGAP ENGINEERING

(75) Inventors: Chaoyin Zhou, Chino, CA (US); Tina T. Salguero, West Hills, CA (US)

(73) Assignee: HRL Laboratories, LLC, Malibu, CA (US)

( * ) Notice: Subject to any disclaimer, the term of this patent is extended or adjusted under 35 U.S.C. 154(b) by 0 days.

(21) Appl. No.: 12/959,197

(22) Filed: Dec. 2, 2010

(51) Int. Cl.
*C07F 7/02* (2006.01)

(52) U.S. Cl.
USPC .............................. 556/400; 257/63; 257/77

(58) Field of Classification Search
USPC ........................... 556/400, 54; 257/29, 77, 63
See application file for complete search history.

(56) References Cited

U.S. PATENT DOCUMENTS

| | | | | |
|---|---|---|---|---|
| 7,635,741 | B2 * | 12/2009 | Niu et al. | 526/281 |
| 7,888,397 | B1 * | 2/2011 | Hibbs et al. | 521/27 |
| 8,110,636 | B1 * | 2/2012 | Fujimoto et al. | 525/471 |
| 2002/0078205 | A1 * | 6/2002 | Nolan | 709/225 |
| 2009/0029221 | A1 * | 1/2009 | Goddard et al. | 429/30 |
| 2009/0240062 | A1 * | 9/2009 | Cho et al. | 548/445 |
| 2010/0028681 | A1 * | 2/2010 | Dai et al. | 428/408 |
| 2010/0038629 | A1 * | 2/2010 | Lazarev | 257/29 |

OTHER PUBLICATIONS

Schultz, M. J. et al; Proceedings of National academy of science (PNAS), May 27, 2008, vol. 205, 21, 7353-7358.*
Website, http://www.cheaptubes.com/graphene.htm, Nov. 22, 2009.*
Boukhvaalov, et al., "Chemical Functionalization of Graphene with Defects",pp. 4373-4379, Nano Letters vol. 8 No. 12, 2008.
Beernink, et al., "Synthesis of Polycyclic Aromatic Hydrocarbons and Graphite Islands via Surface-Induced Reaction of Small Molecules", Chemphyschem, No. 5, pp. 317-320.
Eda, et al.,"Large-area ultrathin films of reduced graphene oxide as a transparent and flexible electronic material", Nature Nanotechnology, vol. 3, pp. 271-274, 2008.
Fan, et al., "Deoxygenation of Exfoliated Graphite Oxide under Alkaline Conditions: A Green Route to Graphene Preparation", Advanced Materials, vol. 20, pp. 4490-4493, 2008.
Forbeaux, et al., "Heteroepitaxial graphite on 6H-SiC (0001): Interface formation through conduction-bad electronic structure", Physical Review, vol. 58, No. 24, pp. 396-434, 1998.
Hernandez, et al. "High-yield Production of Graphene by liquid-phase exfoliation of graphite", Nature Nanotechnology, vol. 3, pp. 563-568, 2008.
Li, et al., "Highly conducting graphene sheets and Langmuir-Blodgett films", Nature Nanotechnology, vol. 3, pp. 538-542, 2008.
Li, et al., "Processable aqueous dispersions of graphene nanosheets", Nature Nanotechnology, vol. 3, pp. 101-105, 2008.
OuYang, et al., "Chemical Functionalization of Graphene Nanoribbons by Carboxyl Groups on Stone-Wales Defects", J. Phys. Chem. C, vol. 112, pp. 12003-12007, 2008.
Ruoff, et al., Preparation and charecterization of graphene oxide paper, Nature, vol. 448, pp. 457-460, 2007.
Simpson, et al., "Synthesis of a Giant 222 Carbon Graphite Sheet", Chem. Eur. J. vol. 8, No. 6, pp. 1424-1429, 2002.
Wang, et al., "Facile Syntehsis and Characterization of Graphene Nanosheets", J. Phys. Chem. vol. C, No. 112, pp. 8192-8195, 2008.
Wang, et al., "Transparent Carbon Films as Electrodes in Organic Solar Cells", Angewandte Chemie, vol. 47, pp. 2990-2992, 2008.
Zhang, et al., "Landau-level Splitting in Graphene in High Magnetic Fields", Physical Review Letters, vol. 96, pp. 1-4, 2006.
Zhi, et al., "A bottom-up approach from molecular nanographenes to unconventional carbon materials", Journal of Materials Chemistry, vol. 18, pp. 1472-1484, 2008.
Zhou, et al., "Substrate-induced bandgap opening in eptaxial graphene", Nature Materials, vol. 6, pp. 770-775, 2007.
Park, "Chemical methods for the production of graphenes," Nature Nanotechnology, vol. 4, Apr. 2009, pp. 217-224 (8 pages)and Corrigendum (1 page).

* cited by examiner

*Primary Examiner* — Sudhakar Katakam
*Assistant Examiner* — Pancham Bakshi
(74) *Attorney, Agent, or Firm* — Ladas & Parry

(57) ABSTRACT

A combination of a substrate selected from silicon, silicon carbide or a metal and a graphene precursor having the following properties: (a) an aromatic structure that forms the basis of the graphene structure, said aromatic structure being selected from the group consisting of: benzene, naphthalene, pyrene, anthracene, chrysene, coronene, and phenanthrene, or a cyclic or acyclic structures which can be converted to aromatic structures and (b) functional groups that can react with each other to form additional aromatic structures.

19 Claims, 4 Drawing Sheets

Z = for example CO₂H, SO₃H, CONH₂, SH, OH, NH₂, NR₃⁺,
SiX₃, Si(OR)₃ (R = alkyl, aryl; X = halide)

METHOD FOR BOTTOM-UP GRAPHENE SHEET PREPARATION AND BANDGAP ENGINEERING

CROSS REFERENCE TO RELATED APPLICATIONS

None

TECHNICAL FIELD

This application describes a method for the preparation of graphene layers. One particular use may be in forming such layers directly on electronically-relevant substrates, such as silicon carbide and silicon, copper, or other materials.

BACKGROUND

"Graphene" is a single layer of carbon atoms in a two-dimensional honeycomb array. This material has been studied intently during the past few years, largely because of its unique property as a ballistic electron conductor. Most of the interest in this field has been focused on developing graphene-based electronics, although other potential applications for graphene and graphene hybrid/composite materials include thermal transport, battery electrode materials, catalyst support, hydrogen storage, etc. Graphene-based electronics should theoretically overcome inherent limitations of state-of-the-art silicon-based electronics. A reliable method for the preparation of graphene layers on electronically-relevant materials is a critical part of development of graphene-based electronics.

Silicon carbide (SiC) is a well-known material for good hardness and chemical stability, and has been pursued for many applications at high power, high frequency, high voltage, and high temperature. It is highly desirable to develop a convenient and stable method to put graphene layers on SiC, among other materials.

Four methods have been used to obtain graphene samples with varying degrees of success. They are chemical exfoliation, mechanical exfoliation, thermal vapor process, and the use of polycyclic aromatic hydrocarbons.

(1) Chemical exfoliation is a solution-based process in which graphite is first oxidized to produce hydroxyl, carboxyl, and epoxide groups on individual graphene sheets so that they then can be exfoliated easily in solution. The graphite oxide product subsequently needs to be reduced and transformed into graphene. However, it has not been possible to remove all the functional groups from graphite oxide, and the remaining oxygen-containing groups and lattice defects degrade the electrical properties of graphite oxide derived graphene compared to pristine graphene. In addition, it is difficult to transfer these graphene sheets onto substrates of interest. Regarding prior art documents, note is made of the following:

a) Ruoff et al., "Preparation and characterization of graphene oxide paper" *Nature* 2007, 448, 457.
b) X Li, G Zhang, X Bai, X Sun, X Wang, E Wang, and H Dai, "Highly conducting graphene sheets and Langmuir-Blodgett films" *Nature Nanotechnology,* 2008, 3, 538.
c) X Fan, W Peng, Y Li, X Li, S Wang, G Zhang, and F Zhang, "Deoxygenation of Exfoliated Graphite Oxide under Alkaline Conditions: A Green Route to Graphene Preparation" *Adv. Mater.* 2008, 20, 4490.
d) G Eda, G Fanchini, and M Chhowalla, "Large-area ultrathin films of reduced graphene oxide as a transparent and flexible electronic material" *Nature Nanotechnology,* 2008, 3, 270.
e) Y Hernandez, et al. "High-yield production of graphene by liquid-phase exfoliation of graphite" *Nature Nanotechnology,* 2008, 3, 563.
f) G Wang, J Yang, J Park, X Gou, B Wang, H Liu, and J Yao, "Facile Synthesis and Characterization of Graphene Nanosheets" *J. Phys. Chem. C* 2008, 112, 8192.
g) D Li, et al. "Processable aqueous dispersions of graphene nanosheets" *Nature Nanotechnology,* 2008, 3, 101.

(2) Mechanical exfoliation removes graphene monolayers from bulk graphite crystals by scraping or a "scotch tape" technique and deposits them onto substrates. This is a highly empirical, low-yielding, and time-consuming process, and again, it is difficult to couple the graphene sheets to the substrate. Regarding the prior art, note is made of the following document:

h) Zhang, et al., "Landau-Level Splitting in Graphene in High Magnetic Fields" *Phys. Rev. Lett.* 2006, 96, 136806.

(3) An annealing process at elevated temperature under vacuum depletes the Si atoms from a SiC surface, resulting in the formation of graphene from all the residual carbon atoms. Graphene from this approach is closely associated with the single crystal substrate, and results have indicated that graphene's electronic properties can change significantly when coupled in this manner compared to isolated graphene sheets (for better or for worse). Like mechanical exfoliation, this method can provide only relatively small graphene samples for fundamental studies, not enough for larger scale applications.

i) Forbeaux, et al., "Heteroepitaxial graphite on 6H—SiC (0001): Interface formation through conduction-band electronic structure" *Phys. Rev. B* 1998, 58(24) 16396.

(4) Polyphenylenes or alkyl-functionalized polycyclic aromatic hydrocarbons have been deposited on Cu(110) or quartz surfaces, respectively, followed by thermally-induced cyclodehydrogenation to form graphene islands or domains of about 5-10 nm.

j) Beernink, G., et al. "Synthesis of Polycyclic Aromatic Hydrocarbons and Graphite Islands via Surface-Induced Reaction of Small Molecules" *ChemPhysChem* 2001, 317.
k) C D Simpson, J D Brand, A J Berresheim, L Przybilla, H J Räder, and K Müllen, "Synthesis of a Giant 222 Carbon Graphite Sheet" *Chem. Eur. J.* 2002, 8, 1424.
l) L Zhi and K Müllen, "A bottom-up approach from molecular nanographenes to unconventional carbon materials" *J. Mater. Chem.* 2008, 18, 1472.
m) X Wang, L Zhi, N Tsao, Z Tomović, and K Müllen, "Transparent Carbon Films as Electrodes in Organic Solar Cells" *Angew. Chem. Int. Ed.* 2008, 47, 2990.

Preliminary indications that the interactions between graphene and silicon carbide substrates can lead to the opening of a semiconductor gap have been published recently. In addition, several computational studies find that the chemical functionalization of graphene should lead to bandgap opening. See:

n) S Y Zhou, et al. "Substrate-induced bandgap opening in epitaxial graphene" *Nature Materials* 2007, 6, 770.

o) F OuYang, et al. "Chemical Functionalization of Graphene Nanoribbons by Carboxyl Groups on Stone-Wales Defects" *J. Phys. Chem. C* 2008, 112, 12003.

p) D W Boukhvalov and M I Katsnelson, "Chemical Functionalization of Graphene with Defects: *Nano Letters* 2008, 8, 4373.

BRIEF DESCRIPTION OF THE INVENTION

The present invention provides a process for the formation of graphene by reactive assembly of large arrays of precursor molecules on a substrate, conversion of these arrays, i.e. large fused arrays of polyphenylenes, to graphene sheets.

Additionally, functional groups may be included in the precursors to facilitate covalently binding the graphene sheet to the substrate whereby the graphene sheet produced may remain adherent to the substrate at the end of the process.

DETAILED DESCRIPTION

Figure 1A:
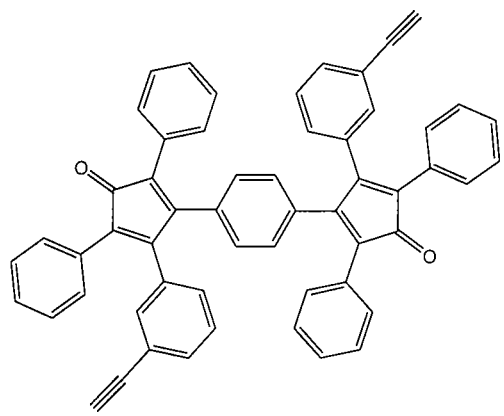
FIG. 1a is an example of a graphene precursor.

Graphene sheets find use both when adherent to a suitable substrate for their electronic properties but also when removed from a substrate, for example, in the production of nanotubes and other similar structures. Suitable substrates, for use when one wishes to produce graphene sheets that remain adherent to the substrate, include: silicon carbide. The use of graphene layers deposited on silicon carbide has been suggested for production of large integrated electronic devices. There have been reports of an anomalous Hall effect when a graphene layer is located on either the silicon surface or the carbon surface of a silicon carbide substrate. Such properties open the way to various opportunities for bandgap engineering. Other substrates to which it may be desirable to bind graphene, because of the electrical properties of the combination, include silicon and metals such as copper. By use of suitable manufacturing techniques, as discussed below, it is possible to deposit graphene only in specific locations on the substrate if this is desired in the light of the intended final use. Other suitable substrates may include metals such as iridium and nickel. Typically graphene does not bond tightly to such metals and their use provides a means for producing separable graphene sheets.

As noted above, a variety of methods to prepare graphene have been developed, albeit each of these methods has some drawbacks. Thus, a major obstacle to progress in this field has been the lack of facile methods to produce graphene sheets, particularly on surfaces needed for electronic applications so that graphene-based nano-structures and devices can be fabricated.

In one aspect, the present invention provides a new method to prepare graphene layers directly on electronically-relevant substrates, such as SiC (0001), as well as Si, Cu, and/or other materials. The basic method consists of two steps: (1) forming one or more layers of polycyclic aromatic hydrocarbon compounds on a suitable substrate by reactive formation from precursor compounds, and (2) the transformation of the polycyclic aromatic hydrocarbon arrays into graphene sheets.

As a second aspect, the present invention provides suitable precursor compounds for use in the above-described method.

The inclusion of anchoring functional groups on the fused/extended polyphenylene arrays will lead to graphene sheets that interact relatively strongly with the substrate surface. These functional groups and their interactions will cause structural changes in the graphene that lead to symmetry breaking and thus the creation of an electronic bandgap.

(1) Molecular Precursor Design and Synthesis

First, precursors are designed to contain the following features:

(a) aromatic compounds (structures) which can be converted into large area of suitable aromatic structures. Suitable aromatic compounds include carbocyclic aromatic compounds including those with fused aromatic rings, for example from one to seven aromatic rings. The examples include: benzene, naphthalene, pyrene, anthracene, chrysene, coronene, phenanthrene, etc. Non-aromatic rings that may be employed which are aromaticized during the production of graphene include: cyclohexane, cyclohexene, tetralin, etc. If particular effects are desired, hetero atoms such as nitrogen, oxygen or sulfur may be present in some of the rings.

(b) reactive groups that can react with each other to form additional aromatic structures or which can link aromatic structures together. These functional groups include, but not limited to, carbon-carbon double bonds, carbon-carbon triple bonds, dienes, ketone, etc.

(c) the precursors have relatively low molecular weight (~100-2000 u) so that they can be vapor deposited or readily dissolved in solvents (d) optionally, the precursor may also contain functional groups to impart particular properties to the graphene produced, for example, to assist in binding to a substrate as described above or to impart particular electronic or steric properties to the graphene sheet. In the case of "functionalized" precursors used to promote binding to a substrate, functional groups that can react with the substrate surface to form covalent bonds, or that can simply interact with the substrate surface by hydrogen bonding, electrostatic attraction, or other non-covalent fashion.

(e) the precursor is designed so to reduce or even eliminate the tendency of aromatic ring structures to stack upon each other ($\pi$-$\pi$ stacking interactions), while increasing the tendency of reactive formation of fused/extended polyphenylene arrays through the reactions between functional groups, which ultimately will lead to predominantly single layer graphene sheets.

Figure 1B:
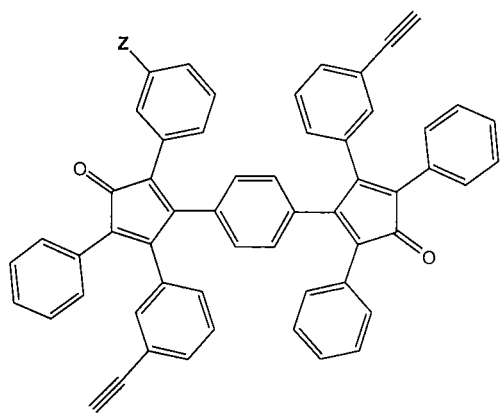
FIG. 1b is another example of a graphene precursor.

The reaction of the functional groups on the structure drives the formation the polyphenylenes on the substrate. An example of such a precursor is shown in FIG. 1a. An example of such a precursor with a substrate-anchoring group Z is shown in FIG. 1b where Z may be COOH, $SO_3H$, $CONH_2$, SH, OH, $NH_2$, $NR_3^+$, $SiX_3$, $Si(OR)_3$, where R=alkyl (such as methyl, ethyl, etc), or aryl (such as phenyl or naphthyl) and X=halide (such as chloro or bromo). If multiple layers of grapheme are desired, they can be produced using precursors with or without a substrate-anchoring group being present. If an anchoring group is present in the precursor this may act as a dopant and facilitate band-gap engineering, although the high temperature processing used may result in loss of some of these groups. As a further alternative, a first layer of grapheme may be formed using precursors containing a substrate anchoring group and then precursors lacking such groups used for the following layers.

FIG. 1a depicts an example of a reactive precursor from which fused/extended polyphenylene arrays can be prepared. FIG. 1b depicts an example of a "functionalized" reactive precursor from which fused/extended polyphenylene arrays that are anchored to the substrate surface can be prepared.

Figure 2:
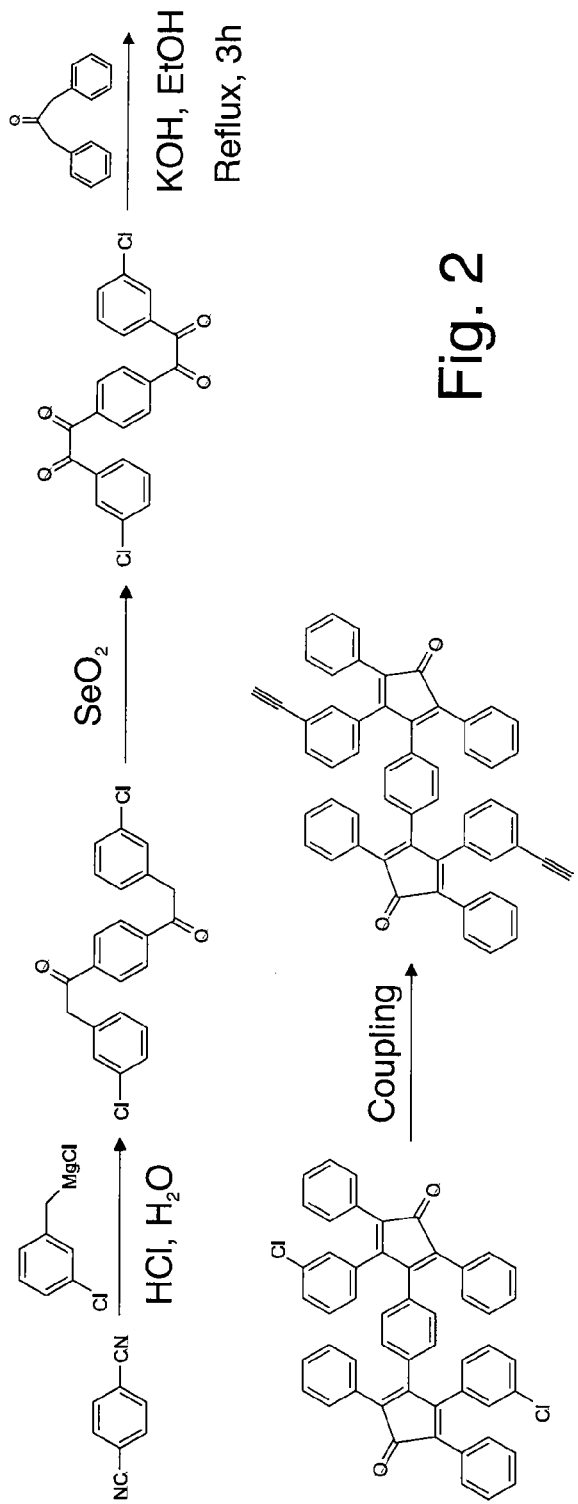
FIG. 2 depicts a synthetic scheme for the preparation of this graphene precursor of FIG. 1a. The graphene precursor of FIG. 1b can be made by an analogous scheme.

The molecules shown in FIGS. 1a and 1b can be synthesized in a typical organic laboratory. For example 1, 4 dicyanobenzene is condensed in an aqueous acid environment with a 3 halo benzyl derivative (for example a Grignard derivative or 3-chlorobenzyl lithium) to produce 1,4-bis(3-chlorophenylacetyl)benzene. This is then oxidized, for example with selenium dioxide, pyridinium chlorochromate or potassium permanganate, to convert the methylene groups of the phenylacetyl moieties to carbonyl groups. The resulting compound may be reacted with dibenzyl ketone, for example, in ethanol in the presence of a strong base such as potassium hydroxide and the resulting product reacted with an alkyne to convert the residual halo groups to ethynyl groups and, if necessary, removing any unwanted substituents subsequently, for example using trimethylsilylacetylene to introduce the ethynyl group and removing the unwanted trimethylsilyl moiety by reaction with anhydrous potassium carbonate. FIG. 2 illustrates a four-step process for the synthesis of the molecule of FIG. 1a. Functional groups to assist in binding the graphene sheet to a substrate as described above may be incorporated into the compound, for example, by using a suitably substituted dibenzyl ketone. The molecule of FIG. 1b can be prepared in an analogous manner.

As an alternative to using starting materials containing a single aromatic ring, compounds containing fused rings may be used. For example instead of using 1,4 dicyano benzene and a 3-cloro benzyl Grignard reagent as starting materials, one can use 2,6-dicayno naphthalene and a Grignard reagent wherein a 1-chloro, an 8-chloro or a 1,8 dichloro naphthalene group replaces the 3-chloro benzene group in the reaction scheme described above.

(2) Reactive Formation of Fused/Extended Polyphenylene Arrays

Figure 3:
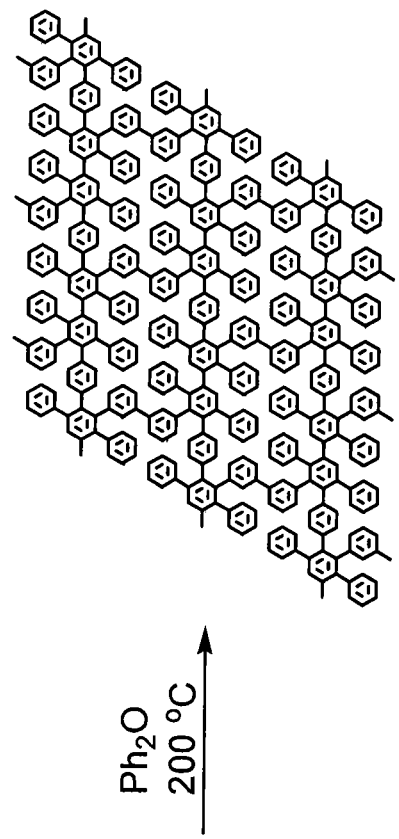
FIG. 3 depicts the reactive formation of fused/extended polyphenylene arrays.
Figure 3:
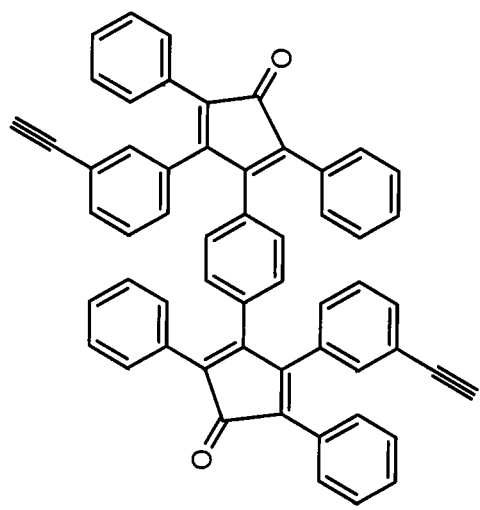

The preparation of graphene sheets occurs through polyphenylene intermediates (see FIG. 3). In the case of this particular precursor, alkyne groups react with cyclopentadienone moieties in an intermolecular Diels-Alder reaction to produce linked phenyl rings. Such a reaction will typically be effected by heating, typically to temperatures in the range 100-300° C., for example. 150-250° C., for example, in the presence of heating medium such as diphenyl ether.

The deposition of this precursor onto the desired substrate and its conversion into polyphenylenes can be accomplished in a solution reaction processes. The polycyclic aromatic hydrocarbon precursor is dissolved in a solvent or a mixture of solvents, and the temperature of substrate is controlled at ~120° C. while the solution temperature is maintained at or near ambient. The reactions usually last for 7-10 days. By this approach, the reaction and deposition of graphene sheets can only take place on substrate. Common organic solvents such as diphenyl ether, tetrahydrofuran, dimethylformamide, o-xylenes, etc. can be used for the reaction.

The reactive formation of polycyclic aromatic hydrocarbon can also be performed in vapor phase. In this approach, a high vacuum of from $10^{-6}$ to $10^{-8}$ torr for example up to $10^{-7}$ torr, a temperature of at least 200° C. commonly at least 300° C., and a prolonged reaction time of more than 10 hours are usually needed. The thermal properties of the precursors are an important consideration, i.e., to make sure that the precursor is stable at the temperature of vaporization. The time of exposure, vacuum, and temperature will determine the number of layers of graphene on the surface. Typically if multiple layers are to be formed a reaction time of five to ten hours per layer is required.

The deposition of precursor will be accompanied simultaneously with the reactive formation of polyphenylene based on the Diels-Alder cycloaddition reaction. The substrate temperature is critical for the deposition and the rate of the reaction. In the solution reaction, the temperature on substrate is maintained at ~120° C. while in vapor deposition, the substrate temperature can be maintained in the range of 100-300° C. for typically 3 to 15 days.

To deposit graphene onto specific locations of the substrate, substrate can be partially masked so that graphene formation is to be avoided during the deposition of precursors. This practice is somewhat similar to the photolithograph process.

(3) Transformation of fused/extended polyphenylene arrays into graphene sheets.

Figure 4:
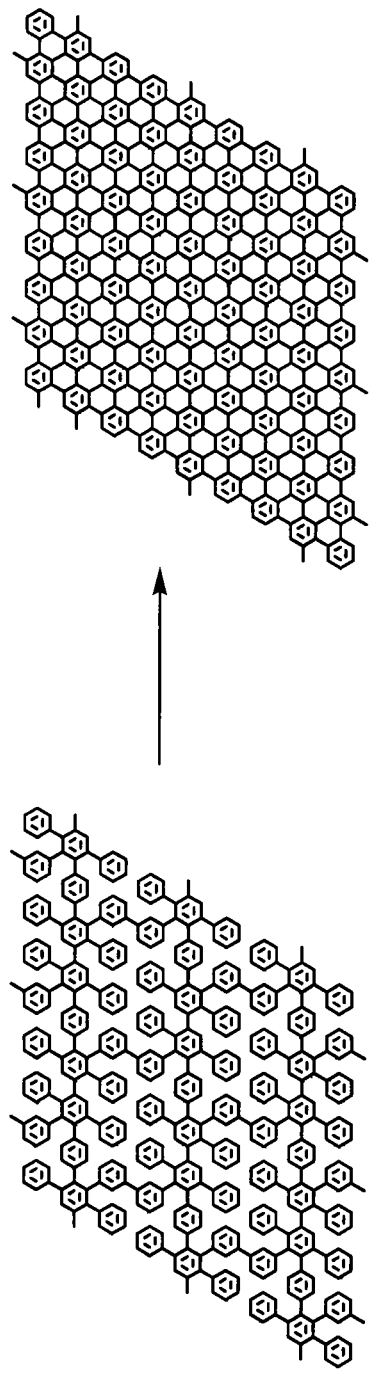
FIG. 4 shows the transformation of a fused/extended polyphenylene array into a graphene sheet.

The polyphenylene arrays will be transformed via cyclodehydrogenation first into fused/extended polycyclic aromatic hydrocarbon arrays and then finally into larger graphene sheets at high temperature, as indicated in FIG. 4. Alternatively, various types of catalysts such as $FeCl_3$/nitromethane, $CuCl_2$ at ambient or slightly higher temperatures such as 50-100° C. can be used to effect this transformation. Typically this temperature range is maintained for 1 to 7 days.

An analogous process utilizing "functionalized" precursor can be used to obtain surface-anchored graphene sheets; and these sheets will contain defect sites where the anchoring functionalities are located.

It should be understood that the above-described examples and embodiments are merely some possible examples of implementations of the presently disclosed technology, set forth for a clearer understanding of the principles of this disclosure. Many variations and modifications may be made to the above-described embodiments of the invention without departing substantially from the principles of the invention. All such modifications and variations are intended to be included herein within the scope of this disclosure and the present invention and protected by the following claims.

What is claimed is:

1. A combination of a substrate selected from silicon, silicon carbide or a metal and a graphene precursor having the following properties:
    (a) an aromatic structure that forms the basis of the graphene structure, said aromatic structure being selected from the group consisting of: benzene, naphthalene, pyrene, anthracene, chrysene, coronene, and phenanthrene, or a cyclic or acyclic structures which can be converted to aromatic structures and
    (b) at least two different types of functional groups that can react with each other to grow the graphene structure by forming additional carbocyclic aromatic structures, wherein the functional group; types are selected from the group consisting of carbon-carbon double bonds, carbon-carbon triple bonds, dienes, ketones, and mixtures thereof.

2. A combination as set out in claim 1 wherein the substrate is silicon carbide.

3. A combination as set out in claim 1 wherein the substrate is copper.

4. A combination as set out in claim 1 wherein the precursor compound containing a moiety convertible into an aromatic structure comprises a cyclohexane, cyclohexene or tetralin moiety.

5. A combination as set out in claim 1 wherein the precursors are suitable for vapor deposition.

6. A combination as set out in claim 1 wherein the precursor contains a functionalized group which can react with the substrate surface to form covalent bonds, or simply interact with the substrate surface in a non-covalent fashion.

7. A combination as set out in claim 6 wherein the functionalized group is selected from the group consisting of group COOH, $SO_3H$, SH, OH, $NH_2$, NHR, $NR_2$, $NR_3^+$, $SiX_3$, $Si(OR)_3$ wherein each R is independently selected alkyl or aryl group and X is halo.

8. A combination as set out in claim 1 wherein the precursor is designed so to reduce or even eliminate the tendency of aromatic ring structures to stack upon each other (π-π stacking interactions), which ultimately will lead to predominantly single layer graphene sheets.

9. A combination of a substrate selected from silicon, silicon carbide or a metal and a graphene precursor wherein the precursor has the structure:

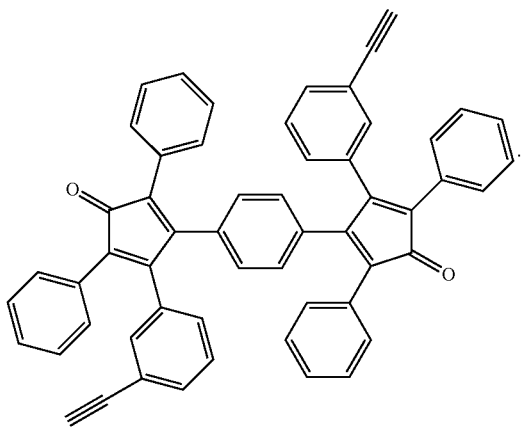 [SMILES: C#Cc1cccc(C2=C(c3ccccc3)C(=O)C(c3ccccc3)=C2c2ccc(C3=C(c4ccccc4)C(=O)C(c4ccccc4)=C3c3cccc(C#C)c3)cc2)c1]

10. A combination of a substrate selected from silicon, silicon carbide or a metal and a graphene precursor wherein the precursor has the structure:

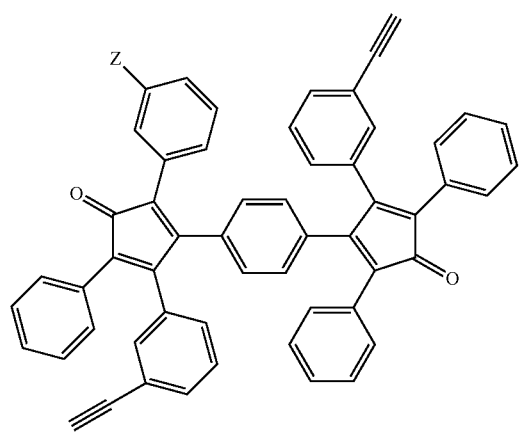

wherein Z is selected from the group COOH, $SO_3H$, SH, OH, $NH_2$, NHR, $NR_2$, $NR_3^+$, $SiX_3$, $SiOR_3$ and wherein each R is independently selected alkyl or aryl group and X is halo.

11. A graphene precursor of the formula:

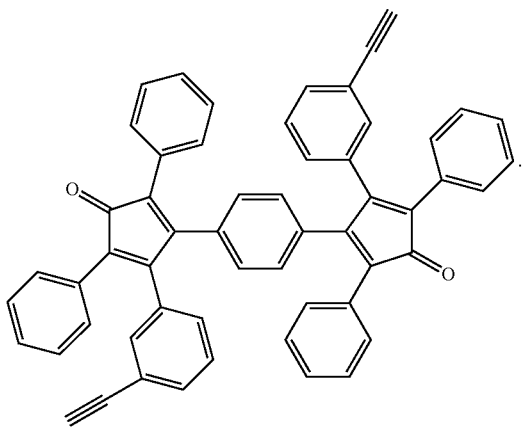 [SMILES: C#Cc1cccc(C2=C(c3ccccc3)C(=O)C(c3ccccc3)=C2c2ccc(C3=C(c4ccccc4)C(=O)C(c4ccccc4)=C3c3cccc(C#C)c3)cc2)c1]

12. A graphene precursor of the formula:

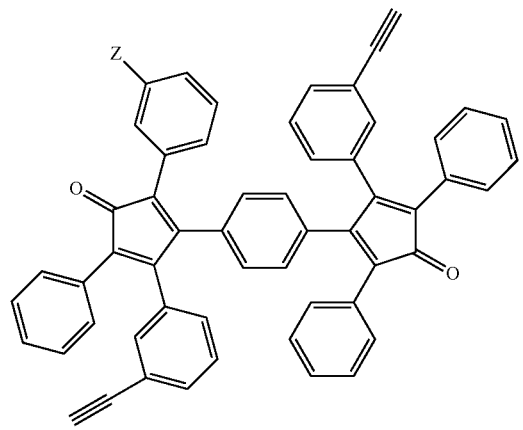

wherein Z is selected from the group COOH, $SO_3H$, SH, OH, $NH_2$, NHR, $NR_2$, $NR_3^+$, $SiX_3$, $Si(OR)_3$ and wherein each R is independently selected alkyl or aryl group and X is halo.

13. A combination as set out in claim 1 wherein the precursors have a molecular weight of from about 100 to about 2,000 u.

14. A combination of a substrate selected from silicon, silicon carbide or a metal and a graphene precursor comprising:
   (a) a carbocyclic aromatic structure that forms the basis of the graphene structure; and
   (b) two or more functional groups of different types that can react with each other to grow said graphene structure by forming additional carbocyclic aromatic structures thereon wherein the functional types are selected from the group consisting of carbon-carbon double bonds, carbon-carbon triple bonds, dienes, ketones, and mixtures thereof
   and wherein said reaction is only between functional groups of different types.

15. A combination as set out in claim 14 wherein the precursor compound containing a moiety convertible into an aromatic structure comprises a cyclohexane, cyclohexene or tetralin moiety.

16. The combination of claim 1, wherein said reaction is only between functional groups of different types.

17. The combination of claim 1, wherein the substrate and graphene combination are present under conditions suitable for vapor deposition wherein the precursor undergoes vapor phase reactive formation of a graphene and simultaneous deposition of the graphene onto the substrate.

18. The combination of claim 17, wherein the conditions for vapor phase deposition comprise a pressure of $10^{-6}$ to $10^{-8}$ torr and a temperature of 100-300° C.

19. A combination as set out in claim 1, wherein the precursors are readily dissolved in solvents.

* * * * *